US007986405B2

(12) United States Patent
Yamashita et al.

(10) Patent No.: US 7,986,405 B2
(45) Date of Patent: Jul. 26, 2011

(54) FOREIGN MATTER INSPECTION METHOD AND FOREIGN MATTER INSPECTION APPARATUS

(75) Inventors: Hiroyuki Yamashita, Fujioka (JP); Mamoru Kobayashi, Hitachinaka (JP); Eiji Imai, Hitachinaka (JP); Yoshio Morishige, Honjo (JP); Koichi Nagoya, Konosu (JP); Hideki Fukushima, Higashichichibu (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 12/758,363

(22) Filed: Apr. 12, 2010

(65) Prior Publication Data
US 2010/0195095 A1  Aug. 5, 2010

Related U.S. Application Data

(63) Continuation of application No. 11/709,858, filed on Feb. 23, 2007, now Pat. No. 7,719,671.

(30) Foreign Application Priority Data

Feb. 24, 2006 (JP) ................. 2006-048133
Feb. 24, 2006 (JP) ................. 2006-048142

(51) Int. Cl.
*G01N 21/00* (2006.01)
(52) U.S. Cl. .............. 356/237.2; 356/237.1; 356/237.5
(58) Field of Classification Search ..... 356/237.1–237.5
See application file for complete search history.

(56) References Cited

U.S. PATENT DOCUMENTS

| 4,893,932 | A | 1/1990 | Knollenberg |
| 5,402,001 | A | 3/1995 | Hagi |
| 5,864,394 | A | 1/1999 | Jordan et al. |
| 6,091,075 | A | 7/2000 | Shibata et al. |
| 6,226,079 | B1 * | 5/2001 | Takeda et al. ............ 356/237.2 |
| 6,384,909 | B2 | 5/2002 | Tomita et al. |
| 6,411,377 | B1 | 6/2002 | Noguchi et al. |

(Continued)

FOREIGN PATENT DOCUMENTS

JP  6-307826  11/1994

(Continued)

OTHER PUBLICATIONS

Japanese Office Action, with English Translation, issued in Japanese Patent Application No. 2007-042228, dated Jun. 28, 2010.

(Continued)

*Primary Examiner* — Tarifur Chowdhury
*Assistant Examiner* — Isiaka O Akanbi
(74) *Attorney, Agent, or Firm* — McDermott Will & Emery LLP

(57) ABSTRACT

In a foreign matter inspection apparatus comprising: irradiating unit for irradiating inspection light to an inspection area of an article to be inspected; intensity detecting unit for detecting intensity of either reflected light or scattered light, which is generated from the inspection area by irradiating thereto the inspection light; position detecting unit for detecting a position of either the reflected light or the scattered light within the inspection area; and deciding unit for deciding whether or not a foreign matter is present within the inspection area; the foreign matter inspection apparatus is comprised of: display unit capable of displaying thereon both a threshold image in which the threshold value is indicated over an entire area of the inspection area, and a detection sensitivity image indicated by being converted from the threshold image.

8 Claims, 9 Drawing Sheets

U.S. PATENT DOCUMENTS

| | | |
|---|---|---|
| 6,597,448 B1 | 7/2003 | Nishiyama et al. |
| 6,683,683 B2 | 1/2004 | Tomita et al. |
| 6,862,491 B2 | 3/2005 | Levin et al. |
| 7,768,635 B2 * | 8/2010 | Nakano et al. .............. 356/237.2 |
| 2001/0030300 A1 * | 10/2001 | Shishido et al. ......... 250/559.44 |
| 2002/0031248 A1 | 3/2002 | Maed et al. |
| 2002/0036769 A1 | 3/2002 | Shimoda et al. |
| 2003/0007677 A1 | 1/2003 | Hiroi et al. |
| 2003/0053676 A1 | 3/2003 | Shimoda et al. |
| 2004/0057044 A1 | 3/2004 | Nikoonahad et al. |
| 2005/0110986 A1 | 5/2005 | Nikoonahad et al. |
| 2006/0109457 A1 | 5/2006 | Miller et al. |
| 2006/0124874 A1 | 6/2006 | Uto et al. |
| 2006/0187446 A1 | 8/2006 | Chang et al. |

FOREIGN PATENT DOCUMENTS

| | | |
|---|---|---|
| JP | 9-74056 A | 3/1997 |
| JP | 11-237344 | 8/1999 |
| JP | 2001-160572 A | 6/2001 |
| JP | 2003-057193 | 2/2003 |
| JP | 2003-177101 | 6/2003 |
| JP | 2003-015164 | 7/2004 |
| WO | WO 2004/063734 A1 | 7/2004 |

OTHER PUBLICATIONS

Japanese Office Action, with English Translation, issued in Japanese Patent Application No. 2007-042251, dated Jun. 25, 2010.

Japanese Office Action, with partial English Translation, issued in Japanese Patent Application No. 2007-042251, mailed Feb. 8, 2011.

* cited by examiner

FIG.5
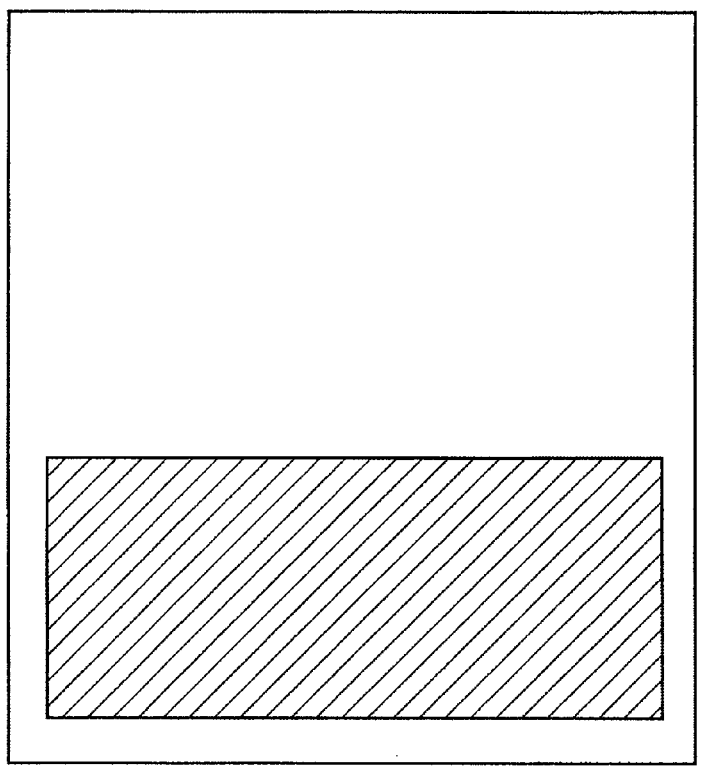
MANAGEMENT VALUE
 LARGER THAN OR EQUAL TO 100 PIECES
 LARGER THAN OR EQUAL TO 10 PIECES

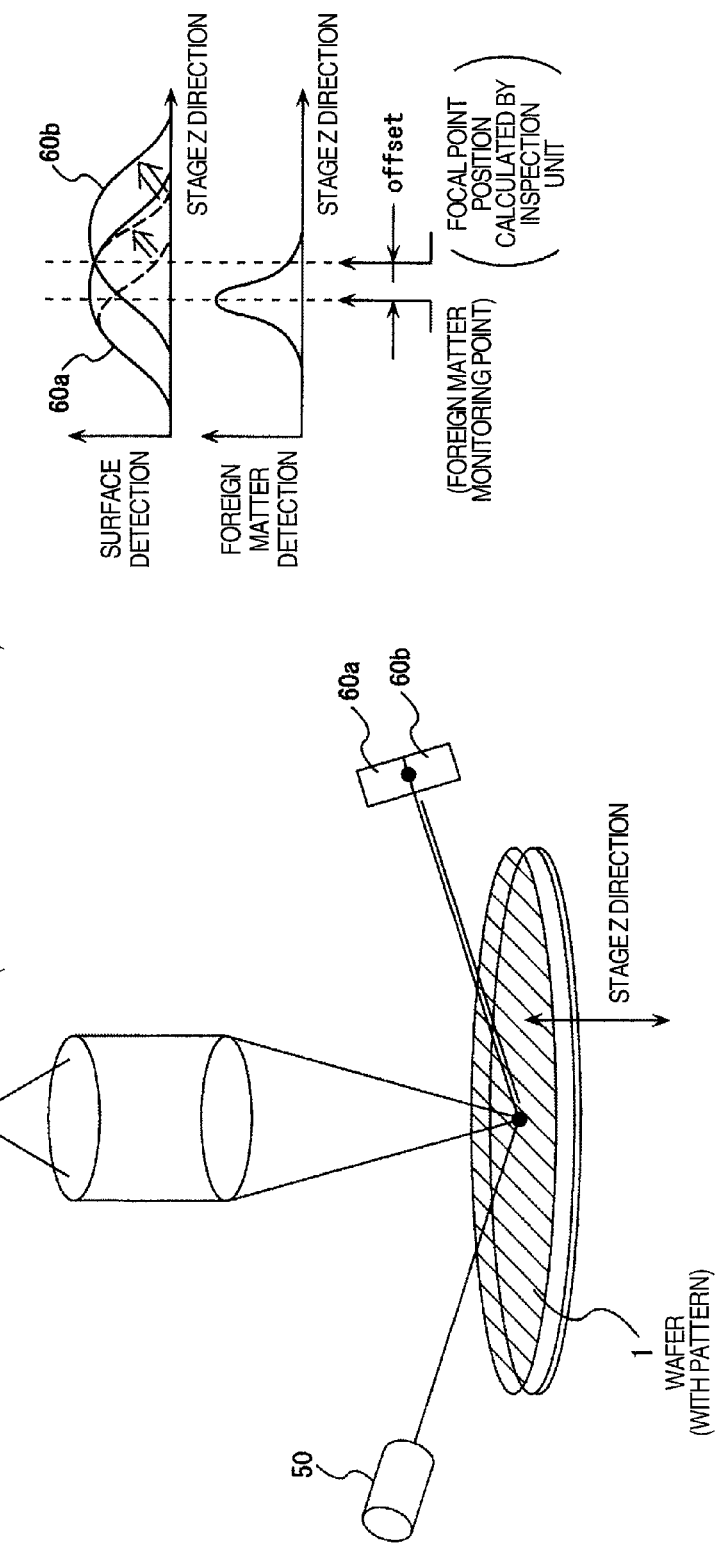

FOREIGN MATTER INSPECTION METHOD AND FOREIGN MATTER INSPECTION APPARATUS

RELATED APPLICATIONS

This application is a Continuation of U.S. patent application Ser. No. 11/709,858, filed on Feb. 23, 2007 now U.S. Pat. No. 7,719,671, claiming priority of Japanese Patent Application Nos. 2006-048133 and 2006-048142, both were filed on Feb. 24, 2006, the entire contents of each of which are hereby incorporated by reference.

BACKGROUND OF THE INVENTION

1. Field of the Invention

The present invention is generally related to a foreign matter inspecting method and a foreign matter inspection apparatus, capable of detecting foreign matters, scratches, defects, contaminations, and the like (these items will be referred to as "foreign matters" hereinafter), which are present on surfaces of inspection matters such as semiconductor wafers (wafers). More specifically, the present invention is directed to a foreign matter inspecting method and a foreign matter inspection apparatus, capable of judging whether or not the foreign matters are present by employing threshold values.

2. Description of the Related Art

In foreign matter inspection apparatuses capable of detecting foreign matters of semiconductor wafers, optical beams such as laser light are irradiated onto surfaces of these semiconductor wafers, and then, either reflected light or scattered light, which are generated from the surfaces of the semiconductor wafers, are detected in order that foreign matters present on the surfaces of semiconductor wafers can be detected.

In such a case where patterns which constitute respective chips have been formed on a surface of a semiconductor wafer, an image signal is formed from intensity of either reflected light or scattered light which are detected; image signals of adjoining chips are compared with each other, or the formed image signal is compared with an image signal as to a good chip which has been previously prepared; and then, when a difference between these image signals is larger than, or equal to a threshold value, it is normally so decided that the detected chip has a foreign matter.

The threshold value is calculated in such a manner that images of all of chips which are arranged along an X-coordinate direction and are detected by a sensor are overlapped with each other, and then, the threshold value is calculated from variations (standard deviation) of images at the substantially same positions within the chips. As a consequence, a judgement is made whether or not a foreign matter is present based upon a lower threshold value at a small variation, and based upon a higher threshold value at a large variation.

An adjustment of the threshold values is related to a yield of products. The yield aspect is described in, for instance, JP-A-2001-160572 and JP-A-9-74056.

Also, a foreign matter inspection apparatus for detecting a foreign matter of a wafer contains a foreign matter detecting system, and a surface detecting system. In the foreign matter detecting system, while an optical beam such as laser light is irradiated onto a surface of a semiconductor wafer, either reflected light or scattered light, which are generated from the surface of the semiconductor wafer, are detected, so that foreign matters present on the surfaces of semiconductor wafers can be detected. The surface detecting system keeps a distance of the wafer surface with respect to the foreign matter detecting system constant.

Conventionally, a distance between an objective lens of a foreign matter detecting system and a surface of a wafer has been assembled and adjusted in such a manner that this distance may becomes a focal distance based upon a designing specification of this objective lens.

Then, while this adjusted condition is continuously maintained under the same condition even in such a case where sorts of wafers to be inspected are different from each other, and manufacturing process steps of semiconductor devices are changed, the inspections have been carried out.

However, as to focal point positions of foreign matter detecting systems, these focal point positions of the foreign matter detecting systems are different from each other depending upon sorts of wafers to be inspected and manufacturing process steps of semiconductor devices. As a consequence, the conventional foreign matter inspection apparatuses have such problems that the detection performance owned by the foreign matter detecting systems cannot be sufficiently reflected, but the detection performance is different from each other, depending to the sorts of wafers and the steps.

SUMMARY OF THE INVENTION

In a foreign matter inspection, as an inspecting system, image signals are formed from intensity of reflected light, or intensity of scattered light which are detected; image signals of adjoining chips are compared with each other, or the formed image signal is compared with an image signal as to a good chip which has been previously prepared; and then, when a difference between these image signals is larger than, or equal to a threshold value, it is so decided that the detected chip has a foreign matter.

In the case of this inspecting system, a threshold value is calculated in such a manner that images of all of chips which are arranged along an X-coordinate direction and are detected by a sensor are overlapped with each other, and then, the threshold value is calculated from variations (standard deviation) of images at the substantially same positions within the chips. As a result, detection sensitivities are different from each other, depending upon variation amounts.

Also, in order that yields are managed, required sensitivities are present with respect to each of areas within a chip. However, there are such problems that there is no indication as to the detection sensitivities for each of the areas within the chip, and management precision is lowered as the yield management information.

The present invention has been made to solve the above-described problems, and therefore, has an object to provide a foreign matter detecting method and a foreign matter detection apparatus, capable of displaying detection sensitivities with respect to each of inspection conditions and each of inspection areas. Also, another object of the present invention is to provide a foreign matter inspecting method and a foreign matter inspection apparatus, capable of setting a management reference with respect to each of the inspection areas, and also capable of increasing precision of yield management.

On the other hand, both surface height positions of wafers (articles to be inspected) which are detected by the surface height position detecting unit (surface detecting systems), and focal point positions of the foreign matter detecting systems are different from each other, depending upon sorts of wafers to be inspected and manufacturing process steps of semiconductor devices.

As to the surface height position detected by the surface detecting system, depending upon sorts of wafers to be inspected and manufacturing process steps of semiconductor devices, the focal point position of the foreign matter detecting system is shifted along either the upper direction or the lower direction. Since the shift amounts are different from each other in accordance with the sorts of wafers and the steps, when recipes are formed, shift amounts are measured, and then, the measured shift amounts must be set to recipe files.

A still further object of the present invention is to provide a foreign matter inspecting method and a foreign matter inspection apparatus, capable of performing proper foreign matter inspections with respect to sorts of wafers and steps, and capable of providing such an information suitable for yield management without lowering foreign matter detection performance.

In a foreign matter inspection apparatus, according to an aspect of the present invention, while images of all of chips arranged along the X-coordinate direction are overlapped with each other, such a threshold value which is calculated from a variation (standard deviation) of images at the substantially same positions within a chip is displayed as a threshold image within one-chip area. Also, from a threshold value level of an area indicated in the threshold image within the one-chip area, resolution within this area is displayed as a detection sensitivity image.

Also, a foreign matter inspection apparatus, according to another aspect of the present invention, is featured by that while an optical beam such as laser light is irradiated onto a surface of a semiconductor wafer, since either reflected light or scattered light is detected which are generated from the surface of the semiconductor wafer, a foreign matter present on the surface of the semiconductor wafer is detected.

In such a case that a pattern which constitutes each of chips has been formed on a surface of a semiconductor wafer, an image signal is formed from intensity of either reflected light or scattered light which are detected; images of all of the chips arrayed along the X-coordinate direction are overlapped with each other; and then, threshold values which are different from each other for every area are displayed as a threshold image within a one-chip area from variation amounts (standard deviation values) of images located at the substantially same positions within the chips (threshold display unit). Also, a detection sensitivity image within one-chip area is displayed from a level of the threshold images within a-chip area for every area. The management reference information for each of the areas can be provided based upon the detection sensitivity image within the one-chip area (resolution display unit). Furthermore, such an information capable of reconsidering both a measuring condition and a measuring manner can be provided with respect to such an area which cannot satisfy the required sensitivity based upon the detection sensitivity image within the one-chip area (re-setting instruction unit).

In accordance with the present invention, the detection sensitivities can be displayed with respect to each of the inspection conditions and each of the inspection areas.

Also, in accordance with another feature of the present invention, the management reference can be set with respect to each of the inspection areas, and the precision in the field management can be increased (management reference setting unit).

Also, in accordance with a further feature of the present invention, in such a foreign matter inspecting method for irradiating inspection light to an article to be inspected which includes a wafer; for receiving light which is reflected, or scattered from the article to be inspected; and for inspecting whether or not a foreign matter present on a surface of the article to be inspected based upon intensity of the received light; a focal point offset can be adjusted in such a manner that the intensity of the received light is emphasized with respect to such a fact as to whether or not a wafer pattern formed on the article to be inspected is present, another fact as to whether or not a film is present, a material of the film, and a thickness of the film. As a result, the proper foreign matter inspection can be realized.

Also, in accordance with a still further feature of the present invention, the focal point offset is adjusted to the surface height position detected by the surface height position detecting unit (surface detecting system) in such a manner that the intensity of the light received by the intensity detecting unit is emphasized. As a consequence, the proper foreign matter inspection can be realized.

Also, in accordance with a further feature of the present invention, since the function for calculating this offset amount is installed in the recipe forming screen, the optimum conditions for the sorts of wafers and the steps can be formed.

In accordance with a still further feature of the present invention, even when the sorts of wafer and the steps are different from each other, the proper foreign matter inspection can be carried out, while the detection sensitivity of the foreign matter is not lowered.

Other objects, features and advantages of the invention will become apparent from the following description of the embodiments of the invention taken in conjunction with the accompanying drawings.

BRIEF DESCRIPTION OF THE DRAWINGS

FIG. 5 is a diagram for illustratively indicating a foreign matter detection upper limit value setting screen for each of areas according to the first embodiment.

FIG. 9A and FIG. 9B are diagrams for illustratively showing a focus offset when a user handles a wafer equipped with a pattern, according to the second embodiment of the present invention.

DETAILED DESCRIPTION OF THE EMBODIMENTS

Figure 1:
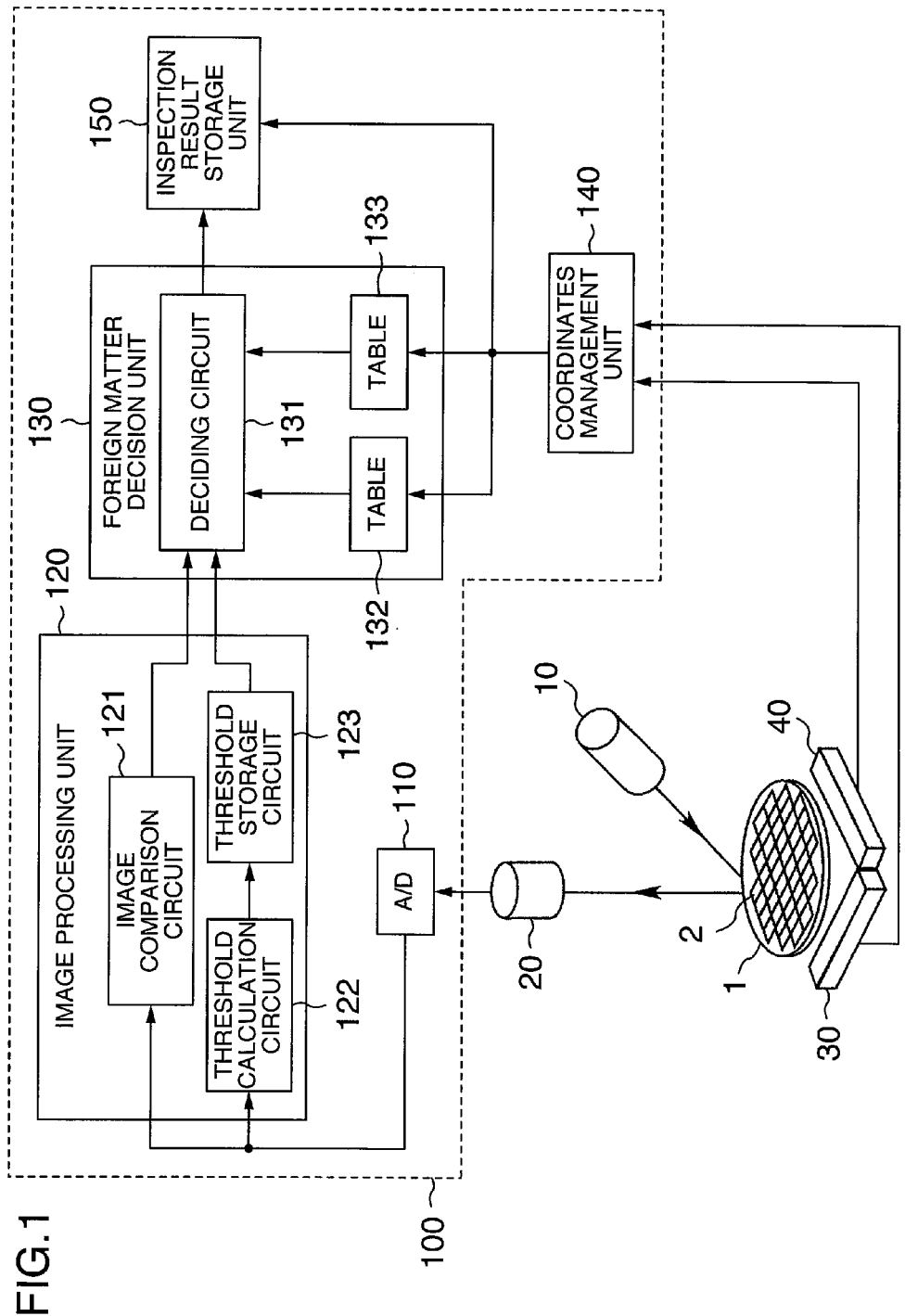
FIG. 1 is a diagram for schematically showing an arrangement of a foreign matter inspection apparatus according to a first embodiment of the present invention.

Next, a description is made of reference numerals used in the present specification. Reference numeral shows a semiconductor wafer; reference numerals 2, 2a, 2b, 2c, and 2d indicate chips; reference numeral 10 represents an illumination unit; reference numeral 20 denotes a detecting unit; reference numeral 30 shows an X scale; and reference numeral 40 indicates a Y scale. Also, reference numeral 100 shows a processing unit; reference numeral 110 indicates an A/D converter; reference numeral 120 represents an image processing unit; reference numeral 121 indicates an image comparison circuit; reference numeral 122 shows a threshold calculation circuit; reference numeral 123 indicates a threshold storage circuit, reference numeral 130 represents a foreign matter decision unit; reference numeral 131 shows a decision circuit; reference numerals 132 and 133 are coefficient tables; reference numeral 140 shows a coordinate management unit; reference numeral 150 indicates an inspection result storage unit; reference numeral 200 shows a stage Z control unit; and also, reference numeral 300 shows an image display unit.

A surface inspection apparatus of the present invention may be applied to flat plane-shaped articles to be inspected such as semiconductor wafers, insulator wafers (for instance, sapphire glass wafer, quartz glass wafer etc.), or glass substrates for liquid crystal panel display devices. In the below-mentioned embodiments, the present invention has been applied to inspections for inspecting foreign matters of semiconductor wafers. That is, embodiments of the present invention will now be described with reference to accompanying drawings.

FIG. 1 is a diagram for schematically indicating an arrangement of a foreign matter inspection apparatus according to a first embodiment of the present invention.

The foreign matter inspection apparatus of the first embodiment is arranged by containing an illumination unit 10, a detecting unit 20 (intensity detecting, unit), an X scale 30, a Y scale 40, and a processing unit 100.

The illumination unit 10 generates a laser light beam having a predetermined wavelength as inspection light, and irradiates this optical laser beam onto a surface of the semiconductor wafer 1 corresponding to an article to be inspected along an oblique direction.

The semiconductor wafer 1 where a chip 2 has been formed on a surface thereof has been mounted on a wafer table (not shown). Since the wafer table is moved along an X direction and a Y direction, the optical laser beam irradiated from the illumination unit 10 is scanned over the surface of the semiconductor wafer 1.

Figure 2:
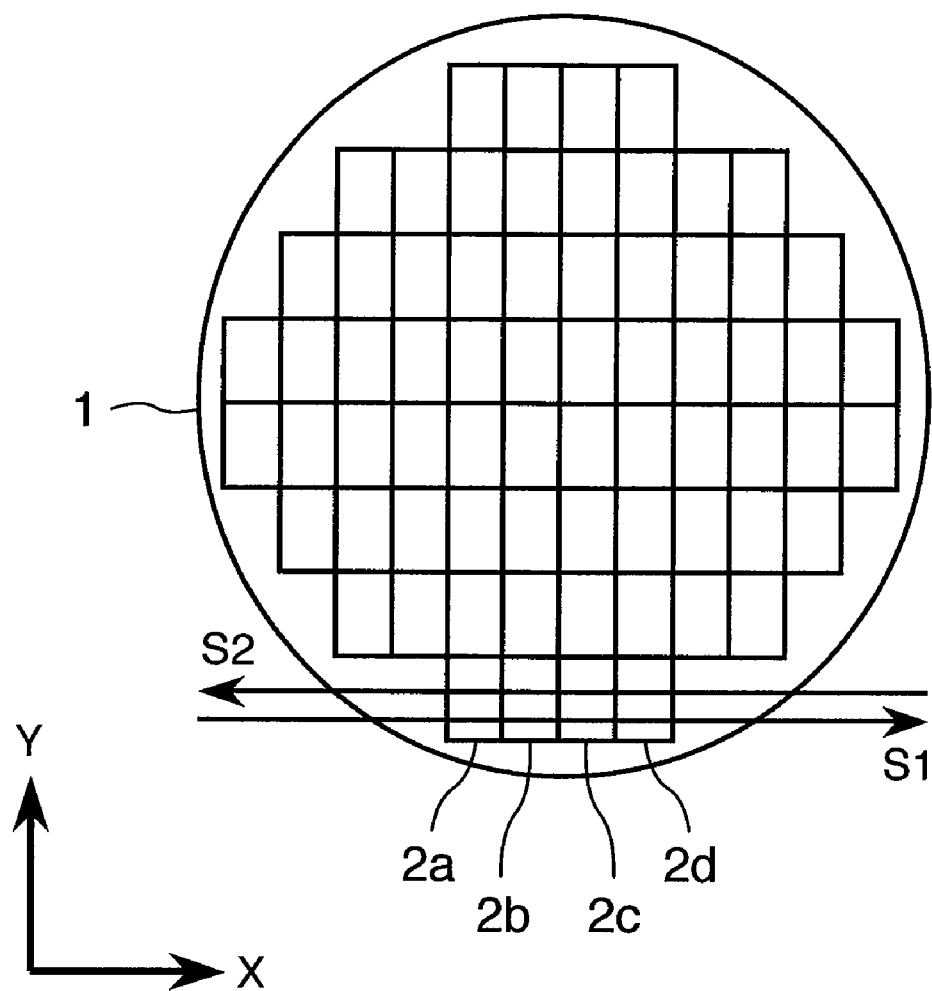
FIG. 2 is a explanatory diagram for explaining a scanning operation of an optical beam by the foreign matter inspection apparatus according to the first embodiment.

FIG. 2 is an explanatory diagram for explaining scanning operations as to the optical beam of the foreign matter inspection apparatus.

When the wafer table on which the semiconductor wafer 1 is mounted is transported along the Y direction, the optical laser beam irradiated from the illumination unit 10 is moved over surfaces of chips 2a, 2b, 2c, and 2d formed on the semiconductor wafer 1 along a direction indicated by an arrow "S1", so that a scanning operation of one line is carried out.

Next, when the wafer table is transported along the X direction, the scanning line is moved along the X direction. Then, when the wafer table is transported in another direction of the Y direction, which is opposite to the above-described scanning direction of the Y direction, the optical beam is moved over the surfaces of the chips 2d, 2c, 2b, and 2a along a direction indicated by an arrow S2, so that a scanning operation of a next line is carried out.

Since these operations are repeatedly performed, the scanning operations are carried out over the entire surface of the semiconductor wafer 1.

In FIG. 1, the optical beam which is irradiated onto the surface of the semiconductor wafer 1 along the oblique direction is scattered by patterns and foreign matters of the surface of the semiconductor wafer 1, so that scattered light is generated.

The detecting unit 20 is constructed of, for instance, a collecting lens, a TDI (Time Delay and Integration) sensor, a CCD (Charge-Coupled Device) sensor, a photomultiplier, and the like. The detecting unit 20 receives the scattered light generated from the surface of the semiconductor wafer 1, and converts intensity of the received scattered light into an electrical signal, and then, outputs the electrical signal to the processing unit 100 as an image signal.

The X scale 30 and the Y scale 40 are constituted by, for instance, a laser scale, and the like. The X scale 30 and the Y scale 40 detect a position of the X direction and a position of the Y direction as to the semiconductor wafer 1 respectively so as to output positional information thereof to the processing unit 100.

The processing unit 100 is arranged by containing an A/D converter 110, an image processing unit 120, a foreign matter decision unit (deciding unit) 130, a coordinates management unit 140, and an inspection result storage unit 150.

The coordinates management unit 140, the Y scale 30, and the Y scale 40, and the like will be referred to as a position detecting unit.

The A/D converter 110 converts the image signal (namely, analog signal) entered from the detecting unit 20 into an image signal (namely, digital signal), and outputs the digital image signal.

The image processing unit 120 is arranged by employing an image comparison circuit 121, a threshold calculation circuit 122, and a threshold storage circuit 123.

The image comparison circuit 121 is arranged by containing, for instance, a delay circuit and a difference detection circuit.

The delay circuit inputs thereinto an image signal derived from the A/D converter 110 so as to delay the inputted image signal. As a result, the delay circuit outputs an image signal of such a chip whose optical beam irradiation has already been accomplished which was irradiated before one-chip to which the optical beam is presently irradiated in the scanning operation shown in FIG. 2.

The difference detection circuit inputs thereinto an image signal derived from the A/D converter 110 and an image signal derived from the delay circuit so as to detect a difference between these image signals, and then, outputs the difference signal. As a result, the image comparison circuit 121 compares the image signals of the adjusting chips with each other.

In such a case where a foreign matter is present on a surface of a chip, scattered light generated from the foreign matter appears as a difference of image signals as to adjoining chips.

It should be understood that the image comparison circuit 121 may be alternatively equipped with a memory instead of the above-described delay circuit, while the memory has previously stored thereinto data as to image signals of good product chips. Then, the image comparison circuit 121 may alternatively compare an image signal of a checked chip with the image signal of the chip as the good product.

The threshold value calculation circuit 122 overlaps an image signal derived from the A/D converter 110 with an image signal derived from the delay circuit every chip, and calculates a variation amount (namely, standard deviation) for each of the substantially same positions within a chip, and then, stores this calculated variation amount into the threshold storage circuit 123.

The foreign matter decision unit 130 is arranged by containing a decision circuit 131 and coefficient tables 132 and 133. Coefficients used to change threshold values have been stored in the coefficient tables 132 and 133 in correspondence with coordinates information.

The coefficient tables 132 and 133 enter thereinto coordinates information supplied from a coordinate management unit (will be explained later) 140 so as to output such coefficients to the decision circuit 131, which have been stored in correspondence with the inputted coordinates information.

In the decision circuit 131, both a threshold value and a difference between image signals of adjoining chips are entered from the image processing unit 120, and also, coefficients used to change the threshold values are inputted from the coefficient tables 132 and 133.

The decision circuit 131 multiplies the threshold value entered from the image processing unit 120 by the coefficients entered from the coefficient tables 132 and 133 so as to form decision-purpose threshold values.

Then, the decision circuit 131 compares a difference of image signals with the decision-purpose threshold values, and when the difference is larger than, or equal to the decision-purpose threshold value, the decision circuit 131 judges that a foreign matter is present, and then, outputs the inspection result to the inspection result storage apparatus 150.

Also, the decision circuit 131 outputs the information as to the threshold value employed in the decision to the inspection result storage apparatus 150.

The coordinates management unit 140 detects both X coordinates and Y coordinates of such a position on the semiconductor wafer 1, onto which the optical beam is presently irradiated, based upon the positional information of the semiconductor wafer 1 entered from the X scale 30 and the Y scale 40, and then, outputs the detected coordinates information.

The inspection result storage unit 150 stores thereinto the inspection result entered from the foreign matter decision apparatus 130 in correspondence with the coordinates information entered from the coordinates management unit 140.

Also, the inspection result storage unit 150 stores thereinto information as to the threshold value entered from the foreign matter decision apparatus in correspondence with either the inspection result or the coordinates information.

With employment of the above-described arrangement, a description is made of a method for displaying a threshold image within one-chip area.

First of all, a preliminary inspection is carried out with respect to one line of the semiconductor wafer 1. At this time, the threshold calculation circuit 122 of the image processing unit 120 calculates a threshold value, and then, the calculated threshold value is stored in the threshold storage circuit 123.

Subsequently, threshold data is read out from the threshold storage circuit 123 so as to display a threshold image of one-chip image (threshold display unit).

It is possible to provide information for re-considering both the measurement condition and the measuring manner with respect to the area which cannot satisfy the required sensitivity from the threshold image of this one-chip image. Alternatively, an instruction for prompting a re-setting operation may be outputted to the image display apparatus 300 based upon this information (re-setting instruction unit).

Figure 3:
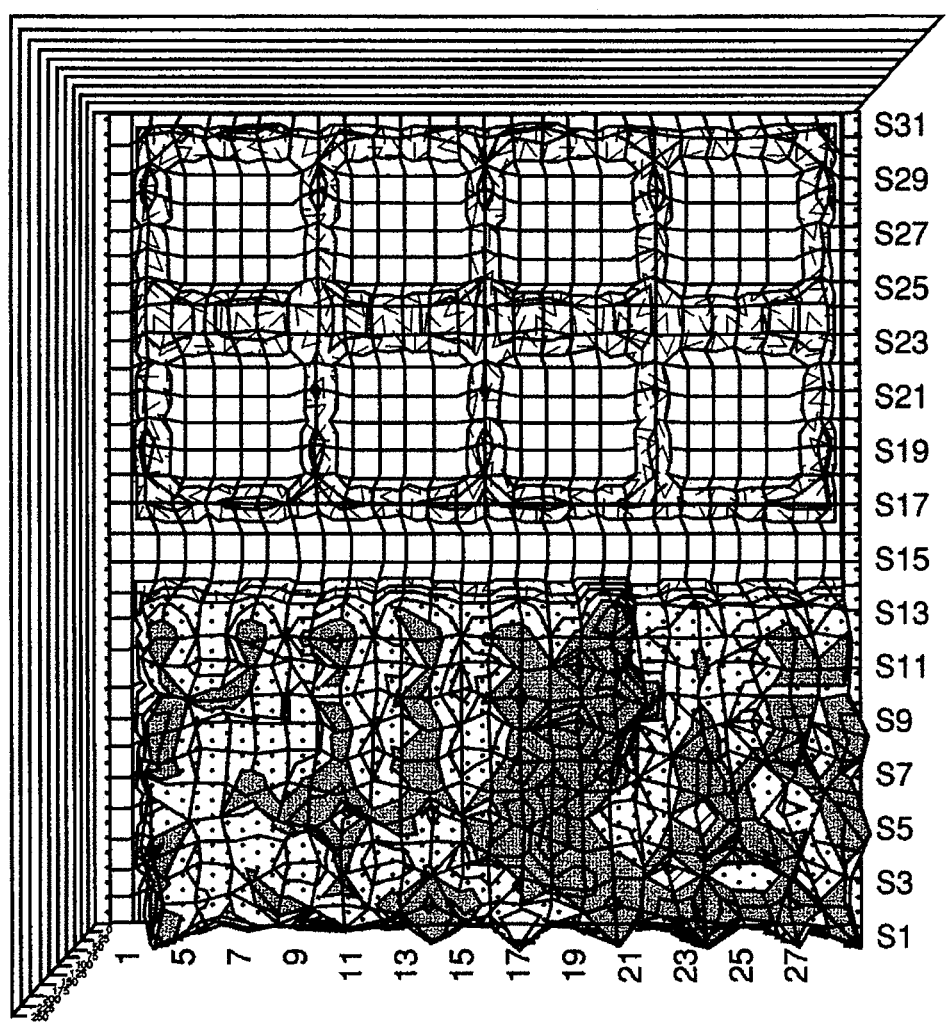
FIG. 3 is a diagram for illustratively representing one example as to a threshold image of a one-chip image according to the first embodiment.

FIG. 3 is a diagram for illustratively showing one example as to the threshold image of the one-chip image.

While a conversion table is employed which has previously been formed from inspection conditions (for example, laser condition, inspection magnification etc.), this threshold image of the one-chip image is converted into a detection sensitivity image of the one-chip image, and then, the converted detection sensitivity image may be displayed (resolution display unit).

In the foreign matter deciding method, a difference image of adjoining chips along the X-coordinate direction is compared with the threshold value of FIG. 3, and then, if the difference image is larger than, or equal to the threshold value, then this difference image is decided as the foreign matter.

As a consequence, at a place whose threshold level is high, a size of a detectable foreign matter becomes large. Conversely, at a place whose threshold level is low, a size of a detectable foreign matter becomes small. A table as to intensity of scattered light and foreign matter sizes is given to a relationship between the detectable foreign matter sizes (resolution) and the threshold values, so that the threshold level of FIG. 3 can be converted into the detection sensitivity of FIG. 4.

It should be understood that the method for calculating the threshold value is carried out as follows: That is, the images of all of the chips arrayed along the X-coordinate direction are overlapped with each other, and then, the variation (standard deviation) of the images at the substantially same positions within the chip is multiplied by an arbitrary coefficient. As a result, the different threshold levels are displayed every area.

Figure 4:
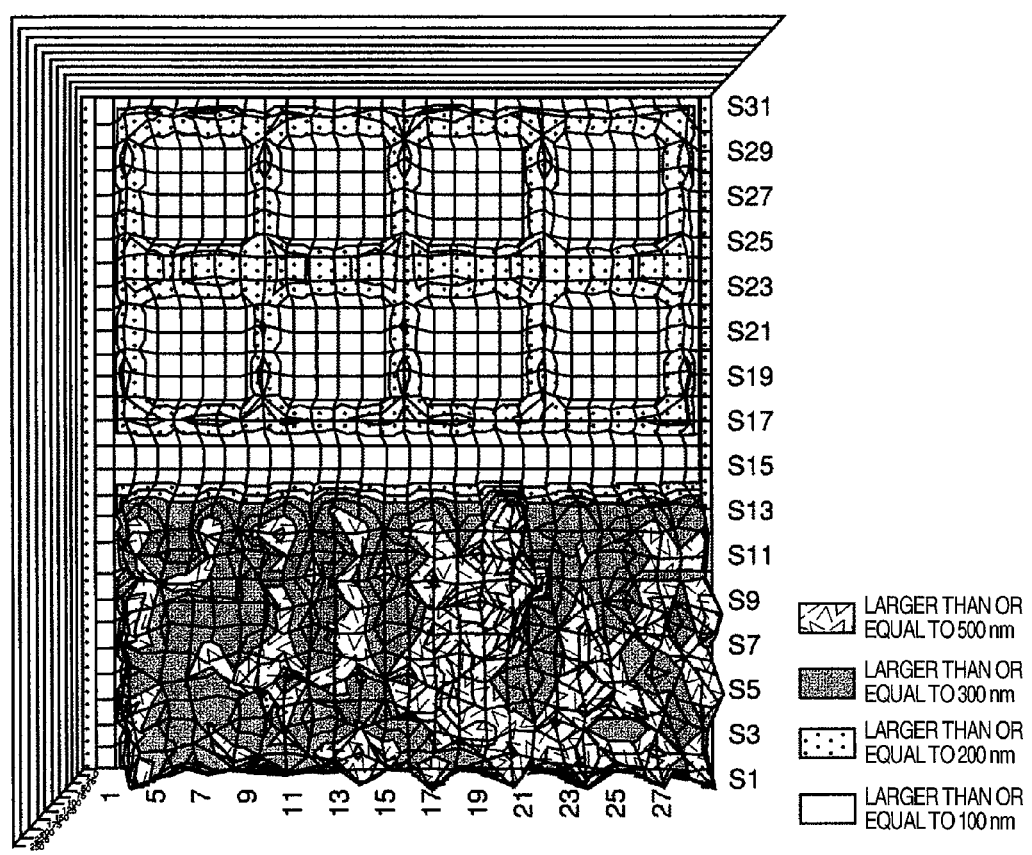
FIG. 4 is a diagram for illustratively showing one example as to a detection sensitivity image of the one-chip image according to the first embodiment.

FIG. 4 is a diagram for illustratively representing one example as to the detection sensitivity image of the one-chip image.

In addition, a foreign matter detection upper limit value may be alternatively set for each of the areas from the detection sensitivity image of the one-chip image (management reference setting unit). Alternatively, it is also possible to manage whether or not each of the chips is good with respect to the foreign matter management reference (good/no good managing unit).

When such an inspection result is obtained which exceeds the set foreign matter detection upper limit for each of the areas, an error may be alternatively displayed (good/no good display unit).

FIG. 5 is a diagram for illustratively showing one example as to a foreign matter detection upper limit value setting screen for each of the areas.

In this first embodiment, the area within the chips of the semiconductor wafer 1 is subdivided into two areas, but the present invention is not limited thereto. Alternatively, an entire inspection area of a semiconductor wafer may be subdivided into three, or more areas in response to sorts and statuses of chips formed therein.

Figure 6:
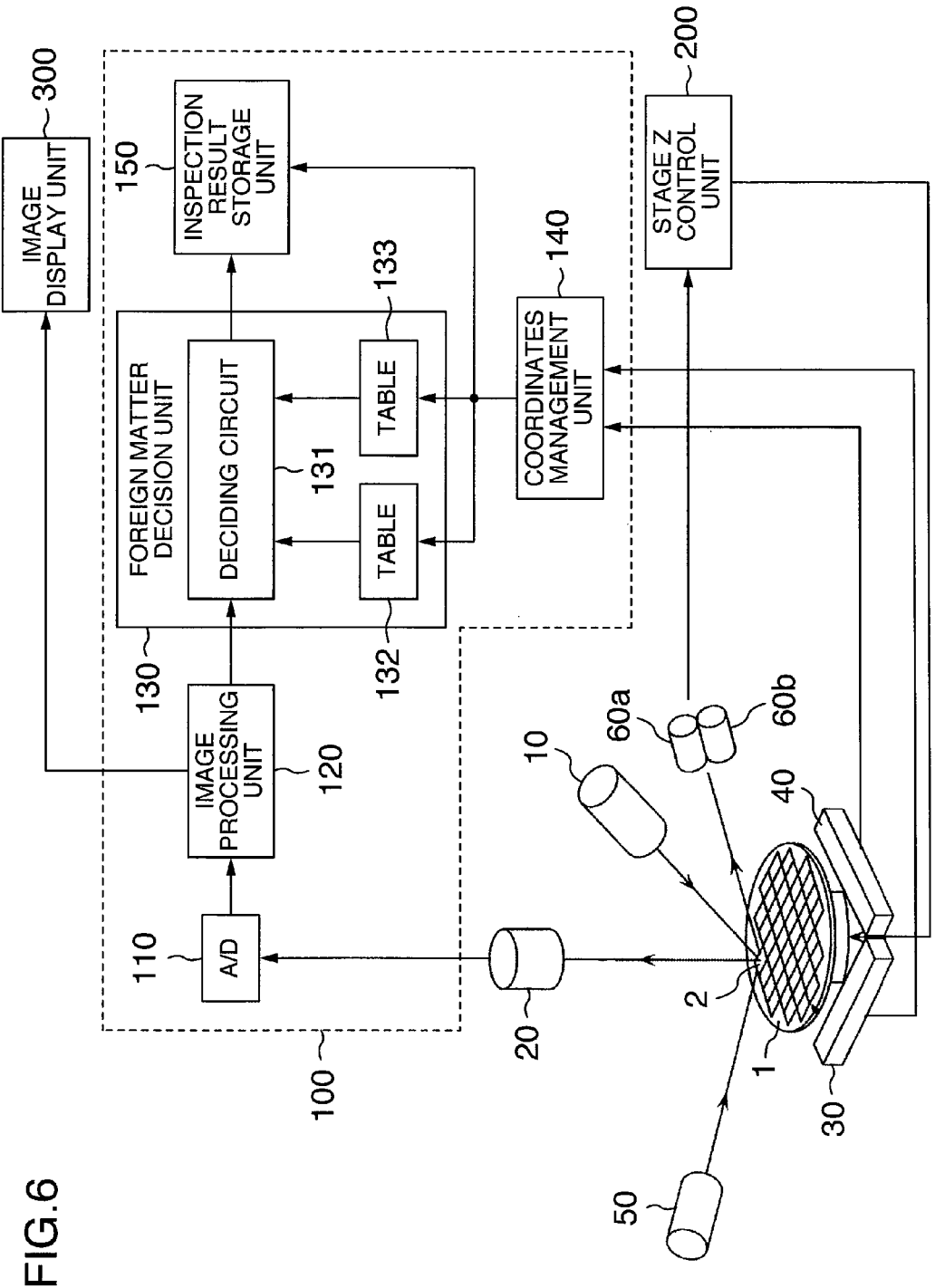
FIG. 6 is a diagram for schematically showing an arrangement of a foreign matter inspection apparatus according to a second embodiment of the present invention.

The display screens such as the threshold image, the detection sensitivity image, and the foreign matter detection upper limit value setting screen as indicated in FIG. 3, FIG. 4, FIG. 5 are displayed on such a display unit as the image display unit 300 which is provided in the foreign matter inspection apparatus and is shown in FIG. 6.

A description is made of a second embodiment of the present invention with reference to accompanying drawings.

FIG. 6 is a diagram for schematically indicating an arrangement of a foreign matter inspection apparatus according to a second embodiment of the present invention.

The foreign matter inspection apparatus of this second embodiment is arranged by containing an illumination unit 10 of a foreign matter detecting system; a detecting unit 20 of the foreign matter detecting system; an X scale 30, a Y scale 40; an illumination unit 50 of a surface height position detecting system; a detector 60 (one set of 2 detectors 60a and 60b) of the surface height position detecting system; a processing unit 100; a control unit 200 of a stage Z; and an image display apparatus 300.

The illumination unit 10 generates a laser light beam having a predetermined wavelength as inspection light, and irradiates this optical laser beam onto a surface of a semiconductor wafer 1 corresponding to an article to be inspected along an oblique direction.

The semiconductor wafer 1 where a chip 2 has been formed on a surface thereof has been mounted on a wafer table, namely a stage Z (not shown). Since the stage Z is moved along an X direction and a Y direction, the optical laser beam irradiated from the illumination unit 10 is scanned over the surface of the semiconductor wafer 1.

A scanning operation of the optical beam by the foreign matter inspection apparatus according to the second embodiment is similar to the above-described scanning operation explained with reference to FIG. 2. That is, when the stage Z on which the semiconductor wafer 1 is mounted is transported along the Y direction, the optical laser beam irradiated from the illumination unit 10 is moved over surfaces of chips 2a, 2b, 2c, and 2d formed on the semiconductor wafer 1 along a direction indicated by an arrow "S1", so that a scanning operation of one line is carried out.

Next, when the stage Z is transported along the X direction, the scanning line is moved along the X direction. Then, when the stage Z is transported in another direction of the Y direction, which is opposite to the above-described scanning direction of the Y direction, the optical beam is moved over the surfaces of the chips 2d, 2c, 2b, and 2a along a direction indicated by an arrow S2, so that a scanning operation of a next line is carried out. Since these operations are repeatedly performed, the scanning operations are carried out over the entire surface of the semiconductor wafer 1.

In other words, since the stage Z is transported along the horizontal direction of the longitudinal and lateral directions, the inspection light can be scanned over the entire surface of the semiconductor wafer 1.

In FIG. 6, the optical beam which is irradiated onto the surface of the semiconductor wafer 1 along the oblique direction is scattered by patterns and foreign matters of the surface of the semiconductor wafer 1, so that scattered light is generated.

The detecting unit 20 is constructed of, for instance, a collecting lens, a TDI (Time Delay and Integration) sensor, a CCD (Charge-Coupled Device) sensor, a photomultiplier, and the like. The detecting unit 20 receives the scattered light generated from the surface of the semiconductor wafer 1, and converts intensity of the received scattered light into an electrical signal, and then, outputs the electrical signal to the processing unit 100 as an image signal.

The X scale 30 and the Y scale 40 are constituted by, for instance, a laser scale, and the like. The X scale 30 and the Y scale 40 detect a position of the X direction and a position of the Y direction as to the semiconductor wafer 1 respectively so as to output positional information thereof to the processing unit 100.

The processing unit 100 is arranged by containing an A/D converter 110, an image processing unit 120, a foreign matter decision unit 130, a coordinates management unit 140, and an inspection result storage unit 150.

The A/D converter 110 converts the image signal (namely, analog signal) entered from the detecting unit 20 into an image signal (namely, digital signal), and outputs the digital image signal.

The image processing unit 120 is arranged by containing, for instance, a delay circuit and a difference detection circuit. The delay circuit inputs thereinto an image signal derived from the A/D converter 110 so as to delay the inputted image signal. As a result, the delay circuit outputs an image signal of such a chip whose optical beam irradiation has already been accomplished which was irradiated before one-chip to which the optical beam is presently irradiated in the scanning operation of the inspection light.

The difference detection circuit inputs thereinto an image signal derived from the A/D converter 110 and an image signal derived from the delay circuit so as to detect a difference between these image signals, and then, outputs the difference signal. As a result, the image processing unit 120 compares the image signals of the adjusting chips with each other.

In such a case where a foreign matter is present on a surface of a chip, scattered light generated from the foreign matter appears as a difference of image signals as to adjoining chips.

It should be understood that the image processing unit 120 may be alternatively equipped with a memory instead of the above-described delay circuit, while the memory has previously stored thereinto data as to image signals of good product chips. Then, the image comparison circuit 121 may alternatively compare an image signal of a checked chip with the image signal of the chip as the good product.

The foreign matter decision unit 130 is arranged by containing a decision circuit 131 and coefficient tables 132 and 133. Coefficients used to change threshold values have been stored in the coefficient tables 132 and 133 in correspondence with coordinates information.

The coefficient tables 132 and 133 enter thereinto coordinates information supplied from a coordinate management unit (will be explained later) 140 so as to output such coefficients to the decision circuit 131, which have been stored in correspondence with the inputted coordinates information.

In the decision circuit 131, both a threshold value and a difference between image signals of adjoining chips are entered from the image processing unit 120, and also, coefficients used to change the threshold values are inputted from the coefficient tables 132 and 133.

The decision circuit 131 multiplies a predetermined value by the coefficients entered from the coefficient tables 132 and 133 so as to form threshold values.

Then, the decision circuit 131 compares a difference of image signals with the threshold values, and when the difference is larger than, or equal to the threshold value, the decision circuit 131 judges that a foreign matter is present, and then, outputs the inspection result to the inspection result storage apparatus 150.

Also, the decision circuit 131 outputs the information as to the threshold value employed in the decision to the inspection result storage apparatus 150.

The coordinates management unit 140 detects both X coordinates and Y coordinates of such a position on the semiconductor wafer 1, onto which the optical beam is presently irradiated, based upon the positional information of the semiconductor wafer 1 entered from the X scale 30 and the Y scale 40, and then, outputs the detected coordinates information.

The inspection result storage unit 150 stores thereinto the inspection result entered from the foreign matter decision apparatus 130 in correspondence with the coordinates information entered from the coordinates management unit 140.

Also, the inspection result storage unit 150 stores thereinto information as to the threshold value entered from the foreign matter decision apparatus 130 in correspondence with either the inspection result or the coordinates information.

The illumination unit 10 of the foreign matter detecting system is referred to as an irradiating unit for irradiating inspection light to an article to be inspected.

The detecting unit 20 of the foreign matter detecting system is referred to as a light intensity detecting unit for receiving light which is reflected, or scattered from the surface of the article to be inspected so as to detect intensity of light.

The illumination apparatus 50 of the surface height position detecting system is referred to as a surface height position detection irradiating unit for irradiating detection light for detecting a surface height position onto the article to be inspected.

The detector 60 (one set of two detectors 60a and 60b) of the surface height position detecting system is referred to as a surface height position detecting unit for detecting a surface height position of the article to be inspected. The surface height position detecting unit contains two detectors, the detecting center positions of which are different from each other along upper and lower directions of the article to be inspected.

The foreign matter decision unit 130 is referred to as a foreign matter deciding unit for inspecting, or deciding whether or not a foreign matter is present on the surface of the article to be inspected based upon light intensity data detected by the light intensity detecting unit.

The control unit 200 controls an upper/lower position varying unit for varying upper/lower positions of the article to be inspected by moving the stage Z along the upper/lower directions.

A description is made of such a case that a threshold value is partially changed in an entire inspection area of the semiconductor wafer 1.

First of all, a preliminary inspection is carried out with respect to the entire surface of the semiconductor wafer 1. At this time, assuming now that all of the coefficient values stored in the coefficient tables 132 and 133 of the foreign matter decision unit 130 are selected to be 1, the deciding circuit 131 performs a deciding operation by employing a constant threshold value. This preliminary inspection may be alternatively carried out with respect to either one sample or several samples. Also, the preliminary inspection may be alternatively carried out for each of the inspections, or in a predetermined interval.

A description is made of a focusing point of the foreign matter detecting system.

a function capable of detecting either reflected light or scattered light, which are generated from the surface of the semiconductor wafer 1, is assumed as the foreign matter detecting system. This foreign matter detecting system has such an arrangement which contains an illuminating unit 10 and a detecting unit 20 such as a lens for collecting either the reflected light or the scattered light. A focal point is made coincident with an optimum surface position of the semiconductor wafer 1 in order to detect a foreign matter. For instance, a surface position of a semiconductor wafer is made coincident with the focal position of the detecting lens. This position is defined as the focal position of the foreign matter detecting system.

A description is made of a focusing position of the surface detecting (surface height position detecting) system.

The beam illumination of the illumination unit 50 of the surface height position detecting system is entered from an oblique direction with respect to the surface of the semiconductor wafer 1, and then, a beam which is reflected on the surface of the semiconductor wafer 1 in a specular reflecting manner is detected by two sets of the photoelectric converting elements 60*a* and 60*b* so as to obtain electrical signals. The angle of this beam illumination, the beam diameter, and the positions of these two photoelectric converting elements 60*a* and 60*b* are arranged in a proper manner, so that the position of the surface of the semiconductor wafer 1 can be detected.

This surface height position detecting function is assumed as the surface detecting system. When the position of the semiconductor wafer 1 is changed along the height direction, detected electrical signals from the two photoelectric converting elements 60*a* and 60*b* become 2 maximum points. An intermediate point where both the signals have the same value is present between two points where these two maximum signals are indicated. This intermediate point is assumed as a focused position of the surface detecting system. This focal point position may be calculated by the foreign matter inspection apparatus.

A description is made of a relationship between surface detecting operations (surface height detecting operations) and foreign matter detecting operations with reference to FIG. 7A, FIG. 7B, FIG. 8A, FIG. 8B, FIG. 8C FIG. 9A, and FIG. 9B.

Figure 7B:
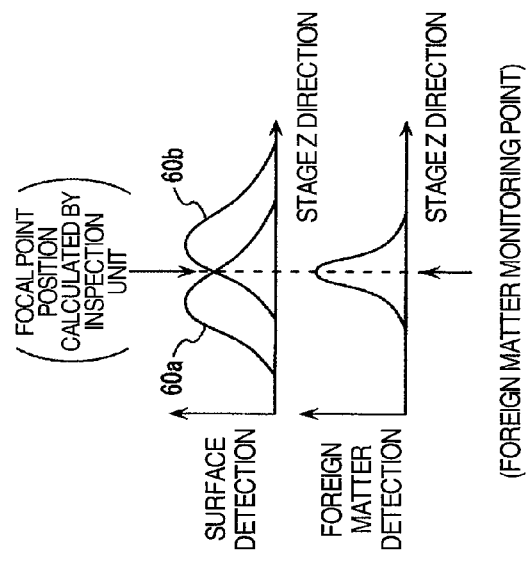
FIG. 7A and FIG. 7B are diagrams for illustratively representing a focusing operation when the foreign matter inspection apparatus according to the second embodiment of the present invention is shipped from a factory.
Figure 7A:
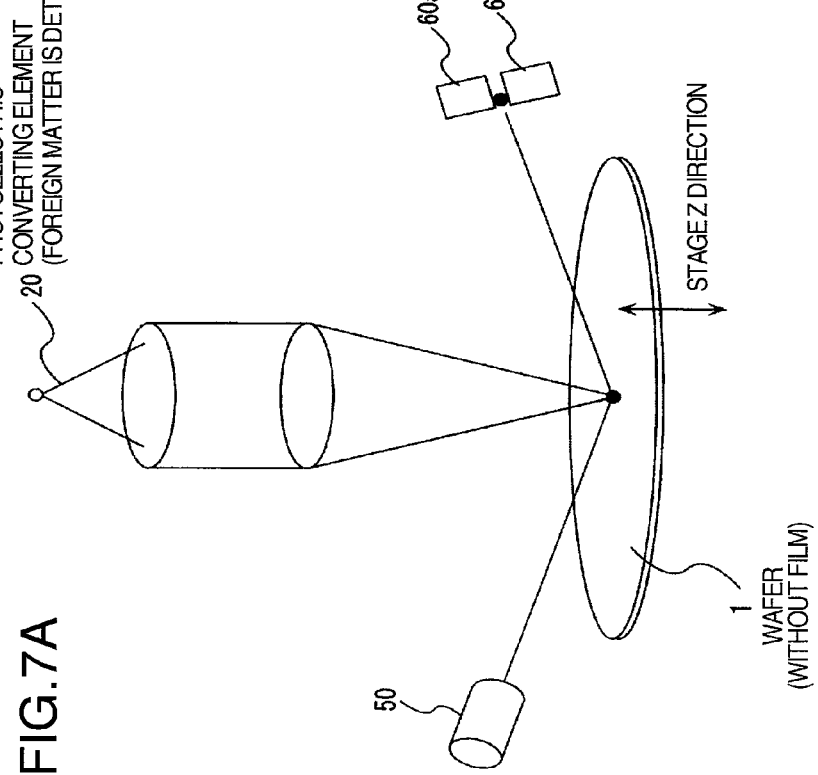

A description is made of an adjusting operation executed when the foreign matter inspection apparatus is shipped from a factory, as indicated in FIG. 7A, and FIG. 7B.

The adjusting operation is carried out by employing such a sample that either a film or a pattern is not formed on the surface thereof such as a silicon wafer.

While a beam illuminating operation of the illumination unit 50 indicated in FIG. 7A is carried out, the semiconductor wafer 1 is transported along the stage Z direction (upper/lower directions) in order to acquire electrical signals detected by the two photoelectric converting elements 60*a* and 60*b*.

As represented in an upper portion of FIG. 7B, two sets of detected electrical signals having maximum values are obtained. An intermediate point between an electrical signal 60*a* whose height position indicates a maximum value on the lower side, and an electrical signal 60*b* whose height position indicates a maximum value on the upper side is calculated as a coincident focal position.

The stage Z is transported along the upper/lower directions in order that a surface (namely, foreign matter monitoring point) of the semiconductor wafer 1 is made coincident with this focal point position. As a result, since the focal point of the detecting unit 20 is made coincident with the surface of the semiconductor wafer 1, an adjusting operation is carried out in such a manner that light receiving intensity of the intensity detecting unit becomes maximum (strongest value).

As previously described, when the foreign matter inspection apparatus is shipped from the factory, the focal point offset adjustment to the focused focal point position is carried out in such a way that the light receiving intensity of the intensity detecting unit is emphasized. As a result, a proper foreign matter inspection can be carried out.

A user performs a foreign matter inspection for also a wafer equipped with a film and a wafer equipped with a pattern.

Figure 8B:
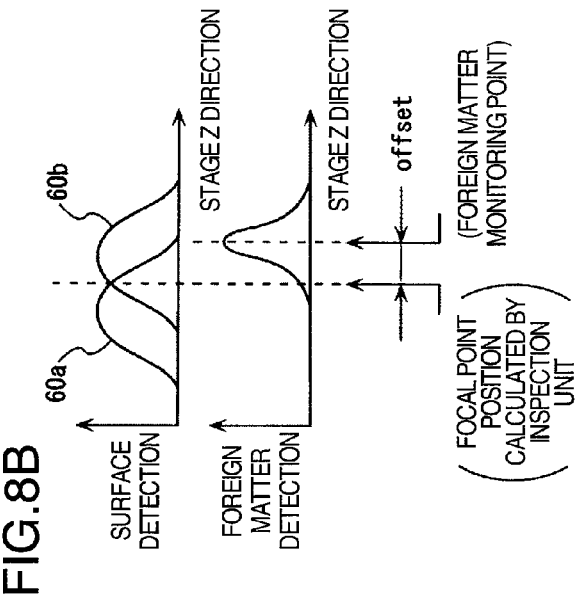
FIG. 8A to FIG. 8C are diagrams for illustratively showing a focus offset when a user handles a wafer equipped with a film, according to the second embodiment of the present invention.
Figure 8C:
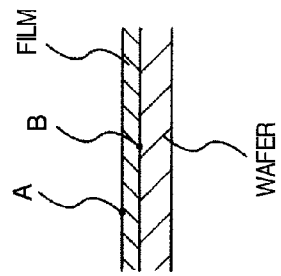
Figure 8A:
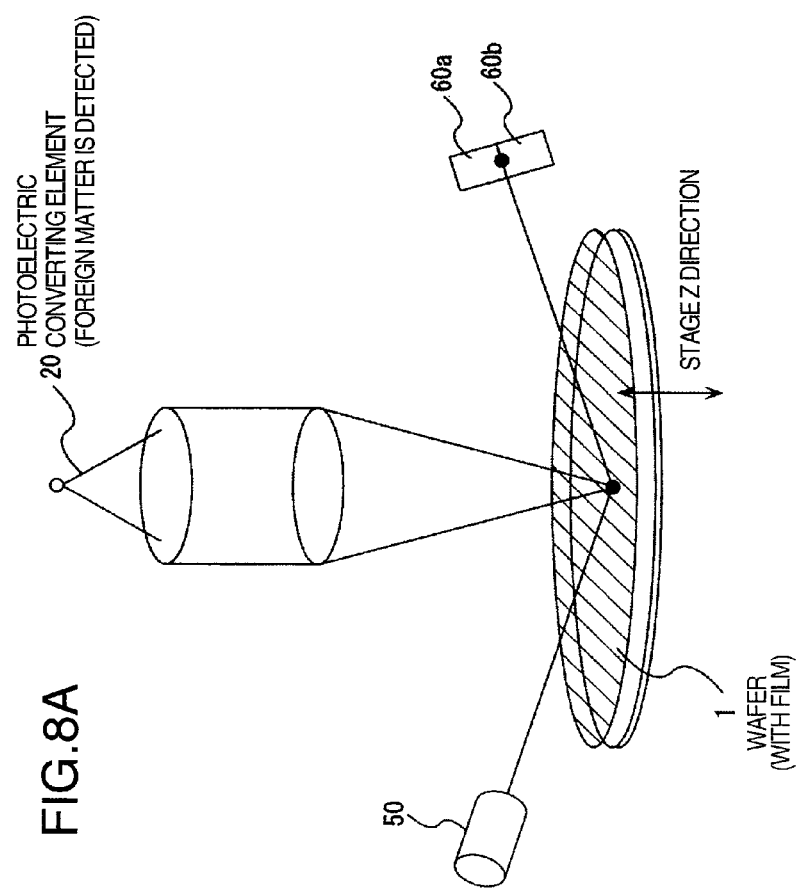

First of all, a description is made of an adjusting operation for a wafer equipped with a film, which is executed on the side of the user and is illustrated in FIG. 8A, FIG. 8B, and FIG. 8C.

In a foreign matter inspection of a wafer 1 equipped with a film shown in FIG. 8A to FIG. 8C, there are many possibilities that the foreign matter inspections are carried out by involving a surface of the film, and a surface of the wafer 1 which is located under side of the film.

In the foreign matter inspection of the wafer 1 equipped with the film, a focal point position detected by the surface detecting system is located at a portion "A" (namely, surface of film) shown in FIG. 8C. In the foreign matter inspection of the wafer 1 equipped with the film, a focal point must be focused on a position of a portion "B". To this end, the wafer 1 is slightly moved along the upper direction. Since this focal point offset adjusting operation is carried out, the focal point position is moved to the surface (namely, foreign matter monitoring point) on the lower side of the film, so that the focal point of the intensity detecting unit is focused, and thus, the intensity of the received light can be emphasized. It should also be noted that this focal point offset value is calculated by a focal point offset calculating unit (will be described later).

Next, in a foreign matter inspection of a wafer 1 equipped with a pattern shown in FIG. 9A and FIG. 9B, such a focal point offset adjusting operation is carried out by which a foreign matter monitoring point is transported from a calculated focal point position to a predetermined position.

As represented in FIG. 9A, in the wafer 1 equipped with the pattern, two pieces of optical beams are generated which are reflected from the pattern surface of the wafer 1 and a portion thereof where no pattern is formed in a specular reflection manner. Electrical signals of the two photoelectric converting elements 60*a* and 60*b* which detect these two optical beams are sensed under such a condition that as indicated in peaks (electrical signals) of 60*a* and 60*b* and in an upper side of FIG. 9B, inclined surfaces of each of the right sides are moved from a dot line position to a solid line position. In other words, summits the peaks (electrical signals) of 60*a* and 60*b* are moved along the stage Z direction, so that the calculated focal point positions are detected at positions which re higher than the original positions.

As a consequence, the position of the wafer 1 is slightly moved along the lower direction from the calculated focal point position. Since this focal point offset adjusting operation is carried out, the surface (foreign matter monitoring point) of the wafer 1 is made coincident with the original focal point position, so that the focal point of the intensity detecting unit is focused, and thus the intensity of the received light can be emphasized. It should also be noted that this focal point offset value is calculated by a focal point offset calculating unit (will be described later).

A description is made of optimization as to a focal point offset.

This optimization may have a specific merit with respect to the wafer 1 equipped with the film and the wafer 1 equipped with the pattern, as explained with reference to FIG. 8A to FIG. 8C, and FIG. 9A to FIG. 9B.

Firstly, a wafer sample is prepared which is wanted to be measured, and then, a general measuring condition is formed in order to measure this wafer sample. As this wafer sample, it is preferable to employ such a wafer 1 equipped with a film, or a pattern, on which PSL (polystyrene latex) has been coated so as to be detected as a foreign matter, depending upon a use field of the adjustment.

While this general measuring condition is used, a foreign matter inspection is carried out, and then, an inspection is obtained. It should also be noted that a focal point offset at this time is selected to be such a value (normally, zero) when the product is shipped. Then, the foreign matter inspection result is displayed as a foreign matter map on the image display apparatus.

One piece, or plural pieces of foreign matter inspection portions of interest are selected by a user operation (inspection area setting unit), and subsequently, a focal point optimization is instructed (focal point optimizing process instructing unit). The foreign matter inspection apparatus receives this focal point optimizing instruction, and thus, performs the below-mentioned process operation.

While the focal point offset is varied with respect to the designated foreign matter inspection portions (position varying unit), an image is acquired (image acquiring unit). In other words, while the stage Z is transported along the upper/lower directions, intensity data of the received light with respect to the respective offset values are acquired by the intensity detecting unit (stage Z is moved along X/Y directions so as to acquire output values of foreign matter detecting sensors in plane shape). In this process operation, a plurality of foreign matter images may be acquired, whose total number is equal to such a number defined by the foreign matter inspection portions X the acquisition times. The portions of the foreign matter inspections are extracted from the foreign matter images, so that illuminance values (intensity of received light) of the foreign matter inspection portions are calculated. Then, a proper focal point offset value for the inspection is acquired from a graph representative of the luminance values with respect to these focal point offset values.

This proper focal point offset value may be defined as, for example, a peak position of the luminance values, or may be defined as such a calculation value which is obtained by performing a multiplication, a division, a subtraction, or an addition of a predetermined coefficient with respect to the value of this peak position. These calculating process operations are carried out by the processing unit 100, and are obtained from a predetermined algorithm (focal offset calculation process unit). Also, the above-described graph is displayed on the image display apparatus 300 such as a CRT, a flat panel display, or the like (luminance value curve display unit).

As previously explained in FIG. 8A to FIG. 8C, and FIG. 9A to FIG. 9B, even in the wafer 1 equipped with the film and the wafer 1 equipped with the pattern, such portions that the intensity of the received light by the light intensity detecting unit becomes maximum can be selected.

In accordance with the above-described first and second embodiments, the proper inspections can be carried out with respect to the sorts of wafers and the steps, and the information suitable for the yield management can be provided while the detecting performance is not lowered. As a result, there is a merit capable of discovering the problem of the process.

Also, the above-described first and second embodiments have exemplified both the foreign matter inspecting method and the foreign matter inspection apparatus with employment of the dark field images caused from the scattered light from the surfaces of the wafers. Alternatively, the present invention may be applied to both a foreign matter inspecting method and a foreign matter inspection apparatus with employment of light field images caused from reflected light from the surfaces of the wafers.

Furthermore, the present invention may be applied not only to an inspection of a wafer, but also may be widely applied to various sorts of inspections as to surfaces of various sorts of objects, for example, scratches, defects, contaminations, and the like.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. An inspection apparatus which inspects a substrate comprising:
   an irradiating unit for irradiating inspection light on an inspection area of said substrate;
   a detecting unit for detecting scattered light from said substrate;
   a first processing unit which calculates a threshold value;
   a second processing unit which inspects a foreign matter of said substrate based on said threshold value; and
   a first display unit which displays a distribution image of said threshold value on said substrate,
   wherein said first processing unit calculates a standard deviation based on said inspection area, and calculates said threshold value by multiplying a coefficient by said standard deviation.

2. An inspection apparatus according to claim 1, wherein said first processing unit calculates said standard deviation by overlapping a plurality of images of a plurality of inspection areas.

3. An inspection apparatus according to claim 1, further comprising,
   a third processing unit which makes a detection sensitivity image of said distribution image.

4. An inspection apparatus according to claim 3, further comprising,
   a second display unit which displays said detection sensitivity image of said threshold value.

5. A method for inspecting a substrate comprising:
   an irradiating step of irradiating an inspection light on an inspection area of said substrate;
   a detecting step of detecting light from said substrate;
   a first processing step which calculates a threshold value;
   a second processing step which inspects a foreign matter of said substrate based on said threshold value; and
   a first display step which displays a distribution image of said threshold value on said substrate,
   wherein in said first processing step a standard deviation is calculated based on said inspection area, and said threshold value is calculated by multiplying a coefficient by said standard deviation.

6. The method according to claim 5,
   wherein in said first processing step said standard deviation is calculated by overlapping a plurality of images of a plurality of inspection areas.

7. The method according to claim 5, further comprising,
   a third processing step of making a detection sensitivity image of said distribution image.

8. The method according to claim 7, further comprising,
   a second display step of displaying said detection sensitivity image of said threshold value.

* * * * *